(12) United States Patent
O'Neil

(10) Patent No.: US 9,968,541 B2
(45) Date of Patent: *May 15, 2018

(54) OPTICAL TREATMENT METHODS

(71) Applicant: ON Light Sciences Inc., Dublin, CA (US)

(72) Inventor: Michael P. O'Neil, Dublin, CA (US)

(73) Assignee: ON Light Sciences Inc., Dublin, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/277,371

(22) Filed: Sep. 27, 2016

(65) Prior Publication Data

US 2017/0027840 A1 Feb. 2, 2017

Related U.S. Application Data

(63) Continuation of application No. 15/201,469, filed on Jul. 3, 2016, now Pat. No. 9,474,707, which is a continuation of application No. 14/832,398, filed on Aug. 21, 2015, now Pat. No. 9,402,817, which is a continuation of application No. 13/753,816, filed on Jan. 30, 2013, now Pat. No. 9,381,167, which is a continuation of application No. 13/436,087, filed on Mar. 30, 2012, now Pat. No. 8,394,359.

(60) Provisional application No. 61/595,065, filed on Feb. 4, 2012, provisional application No. 61/528,130, filed on Aug. 26, 2011.

(51) Int. Cl.

| | | |
|---|---|---|
| A61K 8/70 | (2006.01) |
| A61F 13/40 | (2006.01) |
| A61N 5/06 | (2006.01) |
| A61Q 19/00 | (2006.01) |
| A61B 18/20 | (2006.01) |
| A61Q 1/14 | (2006.01) |
| A61K 31/025 | (2006.01) |
| A61K 41/00 | (2006.01) |
| A61K 8/02 | (2006.01) |
| A61B 18/00 | (2006.01) |
| A61B 17/00 | (2006.01) |

(52) U.S. Cl.
CPC .............. *A61K 8/70* (2013.01); *A61B 18/203* (2013.01); *A61K 8/0208* (2013.01); *A61K 31/025* (2013.01); *A61K 41/00* (2013.01); *A61M 35/006* (2013.01); *A61N 5/062* (2013.01); *A61N 5/0616* (2013.01); *A61Q 1/145* (2013.01); *A61Q 19/00* (2013.01); *A61B 2017/00769* (2013.01); *A61B 2018/0047* (2013.01); *A61B 2018/00458* (2013.01); *A61B 2018/00577* (2013.01); *A61K 2800/81* (2013.01)

(58) Field of Classification Search
IPC .................. A61K 8/70,31/025, 2800/81, 41/00, 8/0208, 18/203, 2017/00769, 2018/00458, 2018/0047, 2018/00577; A61Q 1/145, 19/00; A61N 5/0616, 5/062
See application file for complete search history.

(56) References Cited

U.S. PATENT DOCUMENTS

| | | | |
|---|---|---|---|
| 8,394,359 B1* | 3/2013 | O'Neil | A61B 18/203 424/63 |
| 9,381,167 B2* | 7/2016 | O'Neil | A61K 31/025 |
| 9,402,817 B2* | 8/2016 | O'Neil | A61B 18/203 |
| 9,474,707 B1* | 10/2016 | O'Neil | A61B 18/203 |

* cited by examiner

*Primary Examiner* — Audrea Buckley
(74) *Attorney, Agent, or Firm* — Uradnik Law Firm PC

(57) ABSTRACT

A treatment system and method includes use of a chemical facilitator to provide a result-effective event against one or more negative therapeutic effects related to exposing to a light output a skin portion including a condition treatable in whole or in part with light. In one exemplary embodiment for skin treatment including tattoo removal, perfluorodecalin is used to inhibit or resolve whitening, for example to speed a laser therapy session.

29 Claims, 8 Drawing Sheets

OPTICAL TREATMENT METHODS

RELATED APPLICATIONS

This application is a continuation of, and relates and claims priority to, U.S. patent application Ser. No. 15/201,469, filed Jul. 3, 2016, now pending; which is a continuation of, and relates and claims priority to, U.S. patent application Ser. No. 14/832,398, filed Aug. 21, 2015, now U.S. Pat. No. 9,402,817, issued on Aug. 2, 2016; which is a continuation of, and relates and claims priority to, U.S. patent application Ser. No. 13/753,816, filed Jan. 30, 2013, now U.S. Pat. No. 9,381,167, issued on Jul. 5, 2016; which is a continuation of, and relates and claims priority to, U.S. patent application Ser. No. 13/436,087, filed Mar. 30, 2012, now U.S. Pat. No. 8,394,359, issued on Mar. 12, 2013; which relates and claims priority to: the U.S. provisional patent application Ser. No. 61/528,130 entitled "System and Method for the Treatment of Vascular Lesions," filed on Aug. 26, 2011, by Michael P. O'Neil; and the U.S. provisional patent application Ser. No. 61/595,065 entitled "System and Method for Tattoo Removal," filed on Feb. 4, 2012, by Michael P. O'Neil.

FIELD OF THE INVENTION

The invention relates generally to systems and methods for skin therapy procedures, and more particularly in one exemplary embodiment, to systems and methods including chemical use in one or more treatment processes or steps associated with skin tattoo procedures (e.g., tattoo lightening, part or full tattoo removal), which hereafter may be more generally referred to as "tattoo procedures" or a "tattoo procedure."

In another aspect, the invention more particularly relates to tattoo procedures including use of a chemical to promote treatment.

In another aspect, a chemical delivery process or step may occur (i) before, (ii) after, and/or (iii) concurrently with, use of an emitter or light-generating device for a tattoo procedure (e.g., a laser, a lamp (such as a flash lamp as used in an intense pulsed light (IPL) device or application), or other light output device).

In another aspect, the chemical may be a topical chemical.

In another aspect, the chemical may include a fluorocarbon.

In another aspect, the chemical may include a non-hydrocarbon surfactant.

In another aspect, the chemical may include a fluorosurfactant.

In another aspect, the chemical may include perfluorodecalin.

In another aspect, the invention more particularly may relate to a system or method comprising a sterile device including a chemical.

In another aspect, the sterile device may be a single use device, and the single use device may include a topical chemical.

In another aspect, the sterile device may include one or more of: a fluorocarbon; a non-hydrocarbon surfactant; a fluorosurfactant; and perfluorodecalin.

The above-listed aspects are not necessarily limiting on the invention, nor is one or more of the listed aspects necessarily required in an invention embodiment. The aspects are set forth above without limitation simply to describe the field of the invention.

BACKGROUND OF THE INVENTION

There has been a long felt need for a treatment system and method for tattoos, for tattoo procedures, etc. that is effective without the undesirable side effects of the prior art. There is no universally accepted tattoo treatment. Laser phototherapy (photothermolysis) is perhaps the best treatment regimen available to date for tattoo lightening and removal.

Physicians often use laser phototherapy involving lasers operating at a variety of wavelengths and power and fluence levels. Some physicians prefer Q-switched Nd:YAG lasers operating at 1064 nm. Others prefer typically Q-switched alexandrite lasers operating at 755 nm. Still others prefer dye lasers operating in the visual portion of the spectrum, or, for example, frequency doubled Nd:YAG lasers operating at 532 nm, sometimes described as "KTP lasers", KTP being the crystal which doubles the frequency of the laser. Many other laser types and wavelengths have been used in tattoo procedures as well.

While some favorable treatment results have been achieved, no treatment regimen is without problems. For example, full thickness burns that leave permanent scars have been observed as adverse events following laser phototherapy. Thus, although various devices and techniques have been used, none so far have proven significantly effective.

One reason for problems or adverse events in tattoo treatment may relate to the unpredictable nature of the thermal conversion of oxyhemoglobin ($HbO_2$) and deoxyhemoglobin (RHb) into methemoglobin (metHb). metHb has a much higher optical absorption relative to $HbO_2$ or rHb in the near infrared (NIR) portion of the spectrum thus facilitating thermal runaway once conversion has started. This unpredictable, pseudo-instantaneous conversion is of particular concern in connection with the use of NIR light (i.e., the NIR portion of the spectrum (e.g., around 1064 nm)), which is otherwise desirable for use since NIR light penetrates more deeply into the treatment site than visible light. Use of NIR light thus may permit tattoo treatment to a greater depth, which may result in a better outcome as more of the area or volume including the tattoo portion to be treated can be treated at one time. Prior systems and methods simply are not significantly effective in controlling the thermal conversion of $HbO_2$ and RHb into metHb.

Another reason for adverse events in tattoo treatment using prior systems and methods may be the unpredictable nature of the treatment site. At all wavelengths, including the isosbestic point between $HbO_2$ and RHb (approximately 810 nm), the optical absorption of the blood in the vessels can significantly change in the course of a Q-switched or similar laser pulse. In practical terms, a pulse that is perfectly well tolerated in one location or tattoo portion may induce adverse effects (e.g., burning, scarring, pain, hypopigmentation, hyperpigmentation) in another nearby location or portion. This is because the local scattering, absorption, and/or other properties proximate to the tattoo may change from site to site, which contributes to the uncertainty of the extent of photothermal conversion of $HbO_2$ and RHb into metHb from site to site. Blood treated in the vasculature at one location proximate the tattoo may thermally convert into metHb to a different extent than blood in the vasculature in a different location proximate the tattoo.

A somewhat similar yet separate reason for adverse events in tattoo procedures using prior systems and methods may relate to an unacceptably low level of treatment repeatability. Unwanted uncertainty and results stem from the unpredictability associated with optical and physiological differences across patients. Every patient, every tattoo, etc. is different. An effective set of treatment parameters in one patient may unexpectedly cause an adverse event in another patient with a seemingly identical tattoo or condition. Prior systems and methods simply lack a desired robustness in that they are not significantly effective in controlling factors, e.g., the thermal conversion of $HbO_2$ and RHb into metHb, across individual patients in a treatment group.

One problem, then, in a particular aspect may be viewed as an optical "runaway" effect. Prior systems and methods may be unattractive because this adverse event may occur, for example, as the laser used in treatment is gradually increased in power and/or fluence. As photothermal conversion of one or more hemoglobin species into metHb occurs, suddenly a small change in one or more laser operating parameters or one or more treatment conditions may have a grossly larger effect due to the new presence of metHb. As one example, variations in pressure that the physician applies to a laser hand piece may induce varying degrees of exsanguination, altering the optical properties of a treatment area, and confounding predictability of photothermal conversion. Purpura can result from this effect as well.

Differences in the types of tattoos treated also results in problematic outcomes. Certain tattoo colors (e.g., yellow, green, brown) typically are difficult to treat as compared to other colors (e.g., black) using prior approaches. There is no significantly effective prior system and method applicable to the wide variety of tattoo colors (including difficult to treat colors).

Another problem associated with prior art tattoo procedures is that often such procedures are messy. Typically, debris is ejected from a treatment site, e.g., during laser use. The debris may be solids, liquids, gases, aerosols, and/or other forms of ejecta. Also, with some patients, a treating clinician may be exposed as a result to an unacceptable risk of exposure, e.g., to HIV, hepatitis-C, and/or other infectious diseases. There is no significantly effective prior system and method to help control such ejecta and reduce such adverse risks.

Another problem associated with prior art tattoo procedures may stem from treatment side effects. By way of example, during a laser treatment session, exposure of a treatment area to a laser output may create one or more conditions within the treatment area that tend to reduce the effectiveness of subsequent laser exposures. One example of such side effects is a "whitening" of the area treated.

During tattoo treatment, a "whitening" reaction typically occurs, as evidenced by the formation of bubbles, e.g., in the dermis. The whitening reaction typically occurs immediately upon first laser exposure, with results of the reaction remaining during and after subsequent laser exposures in the same session. The whitening reaction may include, result in, or be caused by, the generation of bubbles or other factors, e.g., due to rapid heating or energy transfer associated with laser exposure, due to laser-induced shock waves, due to microscopically "explosive" cell or other reactions, due to two photon processes (e.g., associated with use of a picosecond or faster laser), etc.

The "bubbles" associated with whitening may be microcavitation bubbles and/or other events and/or circumstances capable of having similar or other negative therapeutic effects, e.g., attenuation of light, light scattering, etc. For convenience only, and without limitation, such bubbles and/or other events and/or circumstances shall be referred to herein individually and collectively as a "bubble" or "bubbles."

Bubbles generally may be located in an area or volume including a portion of the dermis, although other locations are possible too. The bubbles generally may be located in an area or volume including a portion of skin. Heating may be localized, and/or may produce or otherwise cause or promote localized bubble generation. Typically, tissue, skin, tattoo pigment, the dermis portion, etc. are heated during treatment.

It has been observed that a whitening reaction may fade over about twenty minutes or more following the last laser exposure. Such fading may be evidenced by the dissolving of bubbles including gas, or by other factors associated with bubble reduction. Resolution of the whitening reaction may be caused at least in part by the cooling of one or more heated portions.

Whitening is problematic at least in part because the presence of bubbles in the treatment area from a first laser pass may attenuate or weaken the delivery of light in one or more subsequent laser passes. For instance, light impinging on bubbles may scatter in multiple directions, including away from the treatment area. Thus, bubble presence reduces light therapy effectiveness.

Typically, clinicians in tattoo procedures may avoid in part some of the adverse consequences of whitening simply by waiting for the unwanted whitening condition to resolve naturally. Where such a therapy session includes, for example, four laser passes, the total session treatment time (i.e., length of session) may equal about 60-80 minutes or more.

Treatment time, then, often is quite problematic. Typically, prior art tattoo treatment includes, among other things, a single treatment session including multiple (e.g., up to four) laser exposures to a treatment area, with an interval of twenty minutes or more between laser exposures. See, e.g., Kossida et al, Optical tattoo removal in a single laser session based on the method of repeated exposures, J. Am. Acad. Dermatology 2012 feb 66(2): 271-7. Such lengthy treatment time often poses significant problems for patients and clinicians alike. Both clinicians and patients generally would prefer shorter treatment times as compared to such extended periods. This is especially true when multiple treatment sessions are required over a period of months to achieve desired results.

Thus, what is needed is an improved method and system for tattoo treatment that helps predictably and effectively treat tattoos while controlling, reducing, minimizing, and/or eliminating one or more of: (i) the optical "runaway" effect, (ii) system operating or treatment parameter uncertainties, and (iii) one or more other disadvantages that may be associated with prior art systems and methods for treating tattoos (e.g., whitening, attenuation, lengthy treatment times, etc.).

SUMMARY

The present disclosure provides a skin therapy procedure system and method.

In one exemplary embodiment, a tattoo procedure comprising laser therapy including chemical use provides for shorter treatment times. For example, and without limitation, a single tattoo treatment session for tattoo lightening or removal may last only a few minutes, and/or a time interval between successive laser passes may be less than about twenty minutes.

Other benefits and advantages of the present disclosure will be appreciated from the following detailed description.

DETAILED DESCRIPTION

Embodiments of the invention and various alternatives are described below. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of therapeutic events and/or circumstances related to this disclosure. Those skilled in the art will recognize, given the teachings herein, additional such aspects, therapeutic events and/or circumstances related to this disclosure, e.g., additional elements of the dermis, the tissue, and the tattoo; events occurring within the stratum corneum, epidermis, and upper and lower dermal regions; etc. Such aspects related to this disclosure do not depart from the invention, and it is therefore intended that the invention not be limited by the certain aspects set forth of therapeutic events and circumstances related to this disclosure.

Figure 1:
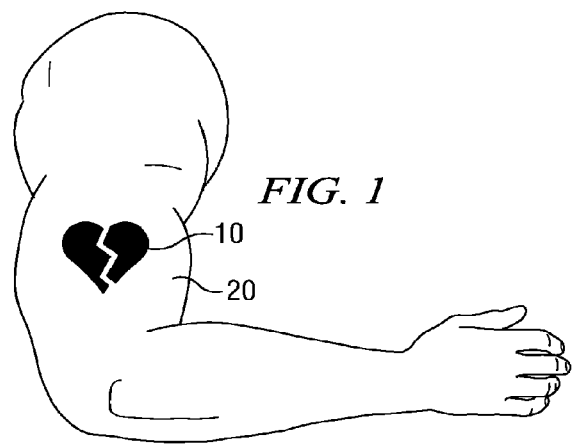
FIG. 1 shows an example of a tattoo on skin.
Figure 2:
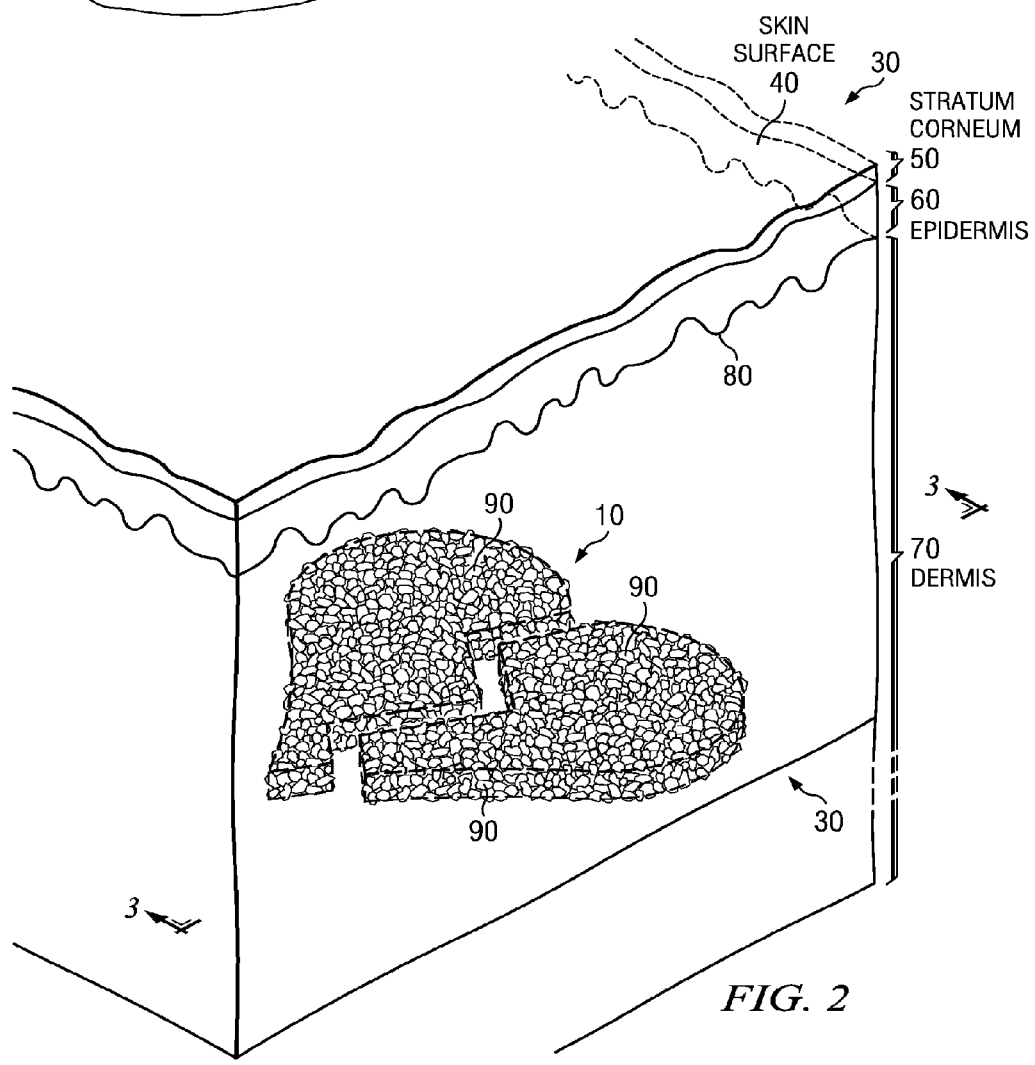
FIG. 2 is an exemplary representation of a treatment area comprising a skin portion including the tattoo of FIG. 1.
Figure 3:
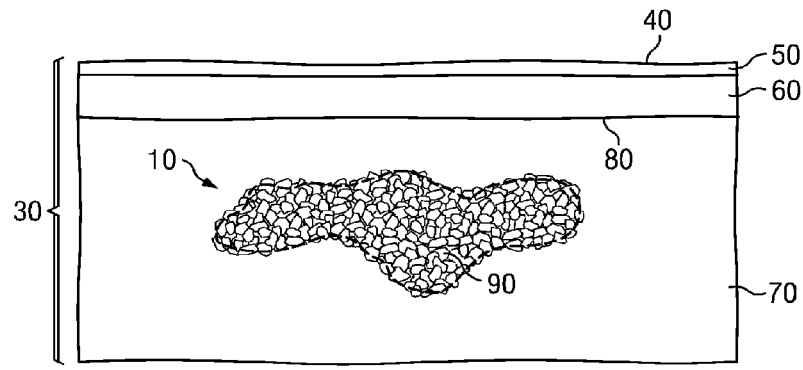
FIG. 3 is a cross-sectional view of the skin portion and tattoo shown in FIG. 2, along the line 3-3 in FIG. 2, as viewed from an angle perpendicular to the cross-sectional plane in the direction indicated by the arrows at line 3-3 in FIG. 2.

FIG. 1 shows an example of a tattoo 10 (i.e., a broken heart) on skin 20. A skin portion 30 including the tattoo 10 is shown in FIG. 2. FIG. 3 is an exemplary cross section of the skin portion 30 and tattoo 10, taken along the line 3-3 in FIG. 2.

Figure 4:
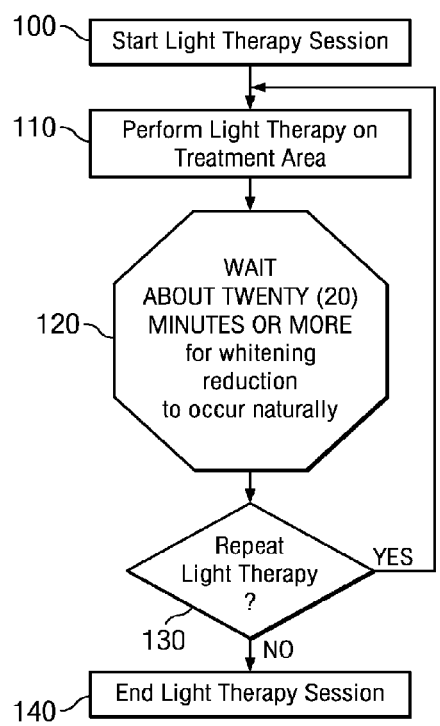
FIG. 4 is a flow chart depicting an exemplary prior art tattoo removal method including a "WAIT" step.

FIG. 4 is a flowchart that illustrates an exemplary prior art tattoo removal laser therapy session. The session includes a method including a "WAIT" step 120. During the treatment session illustrated in FIG. 4, for each laser pass, a waiting period of about twenty minutes or more may be required, to allow time for whitening to resolve naturally.

Referring to FIGS. 2 and 3, tattoos may be located in the dermis 70, below a skin surface 40, the stratum corneum 50, and the epidermis 60 (i.e., located below the D-E junction 80). The location, shape, and overall make up of every tattoo is different. FIG. 2 illustrates that, in general, tattoos may typically reside below the D-E junction 80 in the upper portion of the dermis, and may include a plurality of phagocytosed cells 90 including pigment. The cells 90 naturally migrate slowly, if at all, over time, giving the tattoo a certain degree of permanence.

Although a tattoo may appear to the naked eye to include sharp lines or edges, for most tattoos a closer examination under the skin surface typically reveals otherwise. The surfaces and edges of a tattoo may be quite bumpy or rough, due in part to the imprecision associated with tattoo formation. Thus, a tattoo cross section may have a varying depth, as illustrated for example in FIG. 3.

FIG. 3 shows an exemplary cross section of the tattoo of FIG. 2, taken along the line 3-3, when viewed from an angle that is generally perpendicular to the cross-section face and in the direction indicated by the arrows at line 3-3 in FIG. 2. The tattoo 10 as shown in FIG. 3 includes a plurality of phagocytosed cells 90. The distribution of such cells 90 may vary. The volume including the tattoo may include other features in addition to the phagocytosed cells 90, e.g., an interstitial space between the cells 90. For clarity and convenience only, FIGS. 2, 3, 9A and 10A illustrate an outline of a tattoo portion and phagocytosed cells, and the FIGS. 5A-C, 8, 9B, 10B, 11, 12A-B, and 13A-B illustrate the outline only (although it is and should be understood that such tattoo portions describe and include the phagocytosed cells and other features, despite the absence of any express illustration of the same).

The disclosure relates generally to systems and methods including chemical use in one or more treatment processes or steps associated with skin tattoo procedures (e.g., tattoo lightening, part or full tattoo removal) (which hereafter may be more generally referred to as "tattoo procedures" or a "tattoo procedure").

In another aspect, the disclosure more particularly relates to tattoo procedures including use of a chemical to promote treatment.

In another aspect, a chemical application process or step may occur (i) before, (ii) after, and/or (iii) concurrently with, use of an emitter or light-generating device for a tattoo procedure (e.g., a laser, a lamp (such as a flash lamp as used in an intense pulsed light (IPL) device or application), or other light output device).

In another aspect, the chemical may be a topical chemical.

In another aspect, the chemical may include a fluorocarbon.

In another aspect, the chemical may include a non-hydrocarbon surfactant.

In another aspect, the chemical may include a fluorosurfactant.

In another aspect, the chemical may include perfluorodecalin.

In another aspect, the disclosure more particularly may relate to a system or method including a sterile device including a chemical.

In another aspect, the sterile device may be a single use device, and the single use device may include a topical chemical.

In another aspect, the sterile device may include one or more of: a fluorocarbon; a non-hydrocarbon surfactant; a fluorosurfactant; and perfluorodecalin.

In another aspect, a chemical application process or step may occur (i) before, (ii) after, and/or (iii) concurrently with, use of an emitter or a light-generating device for a tattoo procedure (e.g., a laser, a lamp (such as a flash lamp as used in an intense pulsed light (IPL) device or application), or other emitter), wherein the chemical is: (a) a topical chemical, or (b) not a topical chemical.

In another aspect, the chemical may be a topical chemical including one or more of: (i) a fluorocarbon, (ii) a surfactant, (iii) a fluorosurfactant, and (iv) a non-hydrocarbon surfactant; either alone or in combination.

In another aspect, the topical chemical may include perfluorodecalin.

In another aspect, a tattoo procedure may include one or more applications of light from an emitter or light-generating device to a skin area including a tattoo. More particularly, in tattoo procedures including two or more light applications, one or more chemicals may be applied to a skin area including a tattoo (i) before, (ii) after, and/or (iii) concurrent with, each light application. In one aspect, an applied chemical may include perfluorodecalin and/or one or more other fluorocarbon compounds. In another aspect, application of a chemical may include a topical treatment of such skin area. In another aspect (e.g., in another exemplary embodiment), a chemical may be injected under a skin surface using one or more needles or another delivery device.

In another aspect, a tattoo procedure may include exposing a skin area including a tattoo portion to: (a) one or more applications of light from an emitter or a light-generating device, wherein the time period between light applications is (i) greater than, (ii) less than, and/or (iii) about equal to, twenty (20) minutes; and (b) a topical chemical. The topical chemical may be perfluorodecalin. Where light applications occur in a single session, one or more of the intervals between skin light exposures may be substantially less than about twenty minutes.

In general, a light application may include one or more exposures of a treatment area to one or more emitter light outputs, e.g., one or more laser pulses, lamp pulses, or the like. A treatment area may be exposed to one or more emitter outputs. For example, under circumstances in which an emitter output covers only a portion of an intended treatment area, multiple outputs may be necessary to obtain full treatment. That is, if an emitter output for instance appears relatively small and circular in shape at the surface of the treatment area, clinicians or others may use two or more overlapping outputs, which may be fully or partially overlapping, to treat a larger and/or non-circular tattoo area. Typically, a treatment area may receive or be exposed to sufficient outputs in such manner (e.g., size, placement, strength, time of exposure, etc.) as to achieve a desired therapeutic result. For example, an area may be treated until a desired whitening effect occurs, which may be identified for instance by an observed color change or other result; by achieving a desired evenness of coverage; by achieving a desired completeness of coverage; etc.

For convenience, a group of one or more light applications occurring together in a single time period may be referred to herein as a "treatment session" or a "laser session." Further, and again for convenience, multiple treatment sessions may be identified based upon the amount of time between two or more groups of light applications.

In a case where at least one treatment session includes only one light application (i.e., a group of one) or multiple light applications (i.e., a group of two or more), multiple treatment sessions may be identified by the passage of more than about twenty (20) minutes between one light application group and one or more preceding or subsequent light application groups.

By way of example only, and without limitation, a skin area including a tattoo may be treated by one or more light applications on a first day (i.e., day 1), and one or more light applications on a second day (i.e., day 2) that is different from the first day. In such example, the treatment on day 1 may be regarded as a first treatment session, and the treatment on day 2 may be regarded as a second treatment session. Day 1 and day 2 may be consecutive days, or day 1 and day 2 may be one or more days, weeks, or months apart.

By way of further example only, and again without limitation, a skin area including a tattoo portion may be treated by one or more light applications during a first period (i.e., period 1), and one or more light applications during a second period (i.e., period 2) that is different from the first period. In such further example, the treatment during period 1 may be regarded as a first treatment session, and the treatment during period 2 may be regarded as a second treatment session, provided that the time between period 1 and period 2 is greater than about twenty (20) minutes. For instance, and without limitation, a single day would include multiple treatment sessions when period one occurs during early morning, and period two occurs during afternoon or evening on the same day. Period 1 and period 2 may be consecutive periods spaced more than about 20 minutes apart. Period 1 and period 2 also may be spaced days, weeks, or months apart.

In general, multiple treatment sessions may be identified by the passage of an amount of time between groups of light applications that is more than about twenty (20) minutes; and, in accordance with an exemplary embodiment of the disclosure, the approximate amount of time of at least one treatment session including multiple light applications may be less than about twenty minutes multiplied by the number of light applications in the session.

During tattoo treatment, a "whitening" reaction occurs, as evidenced for instance by the formation of bubbles, e.g., in the dermis. The whitening reaction typically occurs immediately upon first laser exposure, with results of the reaction remaining during and after subsequent laser exposures in the same session. It has been observed that the whitening reaction and/or its results fade over about twenty minutes following the last laser exposure, as evidenced for example by the dissolving of gas bubbles. Other factors may cause bubble reduction. The whitening reaction may include, result in, or be caused by, the generation of bubbles or other factors, e.g., due to rapid heating or energy transfer associated with laser exposure, laser-induced shock waves, microscopically "explosive" cell or other reactions, two photon processes (e.g., associated with use of a picosecond or faster laser), etc. The bubbles may be micro-cavitation bubbles. The bubbles generally may be located in an area or volume including a portion of the dermis. The bubbles generally may be located in an area or volume including a portion of skin.

A "whitening" or "whitening reaction" in one aspect refers to any event or combination or sequence of events, alone or in combination, causing a negative therapeutic effect resulting from exposure of a treatment area to a light output (e.g., a laser output). The events, alone or in combination, in sequence or not, may include a chemical reaction (or not); a physical change (or not); and/or one or more chemical reactions (or not) and physical changes (or not), either alone or in combination. In one aspect, then, this disclosure describes a skin treatment method, including: (a) exposing to a light output a skin portion including a condition treatable in whole or in part with light; and (b) providing an amount of a chemical facilitator sufficient to provide a result-effective event against a negative therapeutic effect, e.g., related to step (a), of performing the skin treatment method, related to the skin treatment method, etc. The result-effective event can be a single event, and/or a sequence or combination of events, and may include a chemical reaction (or not); a physical change (or not); and/or one or more chemical reactions (or not) and physical changes (or not), either alone or in combination. For tattoo removal, one example of a negative therapeutic effect is bubble formation in the dermis. There are, of course, other negative therapeutic effects that one of ordinary skill in the art, having the benefit of this disclosure, will recognize for the one or more types of light output of particular interest (for tattoo removal, skin treatments, and/or for other applications). A result-effective event against a negative therapeutic effect may counter one or more negative therapeutic effects or events, alone or in combination. The result-effective event may include one or more occurrences that, alone or in combination, may counter such negative therapeutic effect or event in one or more ways, either alone or in combination, e.g., prevention, resolution, reduction, inhibition, neutralization, avoidance, amelioration, blockage, forestalling, interruption, obstruction, prohibition, stoppage, acting, accelerating, breaking down, solving, advancing, expediting, stimulating, removing, pacing, controlling, causing, generating, speeding, warming, cooling, facilitating, urging, checking, slowing, etc. There are, of course, additional such ways beyond those listed which will be apparent to one of ordinary skill in the art having the benefit of this disclosure.

In one embodiment, a chemical facilitator sufficient to provide a result-effective event against a negative therapeutic effect is provided, or a facilitating step is performed, as one one or more distinct events at $t_1, t_2, t_3, \ldots, t_n$, where each event at $t_1, t_2, t_3, \ldots, t_n$, etc. is defined using a therapeutic reference scale. A therapeutic reference scale may be anything of interest to a physician, clinician, or other caregiver related to the patient and therapy involved. Exemplary therapeutic reference scales include, without limitation: time, presence or absence of a condition, occurrence of an event, etc. Note, too, that each event at $t_1, t_2, t_3, \ldots, t_n$ may be defined using the same or different therapeutic reference scales; related or unrelated therapeutic reference scales; etc.

During a tattoo procedure, heating may be localized, and/or may produce or otherwise cause or promote localized bubble generation. Typically, tissue, skin, tattoo pigment, the dermis portion, etc. are heated during treatment. Resolution of the whitening reaction may be caused at least in part by the cooling of one or more heated portions. Thus, in one exemplary aspect, an exemplary embodiment of the invention may include a cooling step or process before, during, or after light exposure, chemical application, etc., to provide cooling related to the treatment (e.g., cooling of the skin, the dermis, the treatment area, a chemical, an applicator for light, an applicator for a chemical, an emitter output delivery system, a bandage, a patch, a skin contact device, etc.).

Again, whitening resolution typically occurs over time following laser exposure. It has been shown that whitening reaction resolution over about twenty minutes or more following laser exposure may prove advantageous, particularly where such 20-minute period is immediately followed by one or more laser exposures (with a similar 20-minute resolution period following each such laser exposure). Such process including 20-minute intervals between laser passes may be referred to by some as the "R20" method. The R20 method has significant drawbacks, however. For example, use of the R20 technique (e.g., including four laser passes) may require up to eighty minutes (or more) of treatment time per treatment session, which is impractical. Thus, there has been a substantial and long felt need for a treatment system and method for tattoos that is effective in shorter sessions.

Figure 5A:
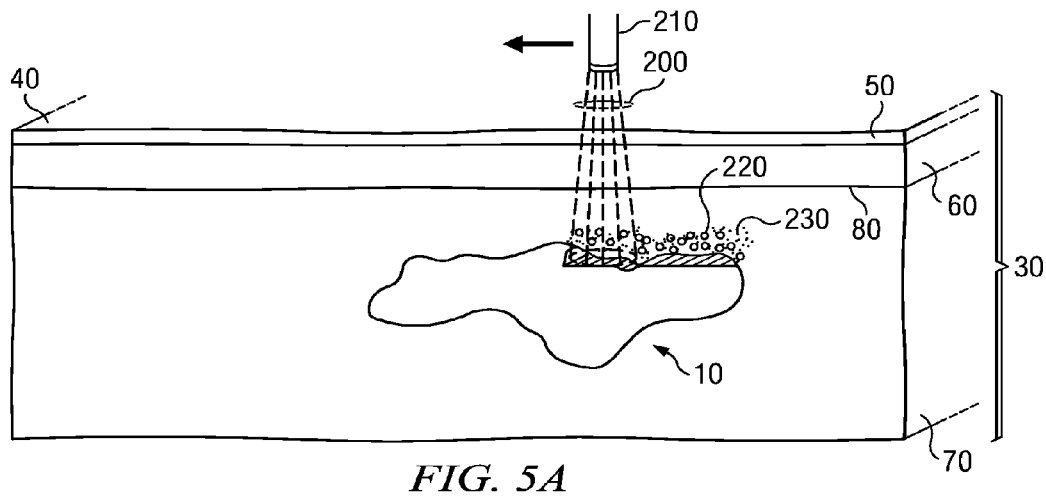
FIG. 5A is an illustration of an exemplary laser pass treating the tattoo shown in FIG. 3
Figure 5B:
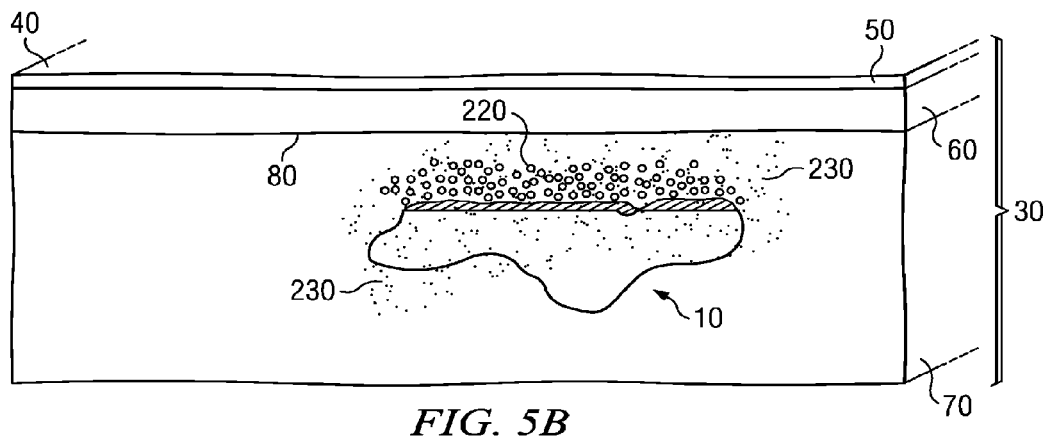
FIG. 5B is an illustration of the tattoo shown in FIG. 3 immediately following the exemplary laser pass illustrated in FIG. 5A.
Figure 5C:
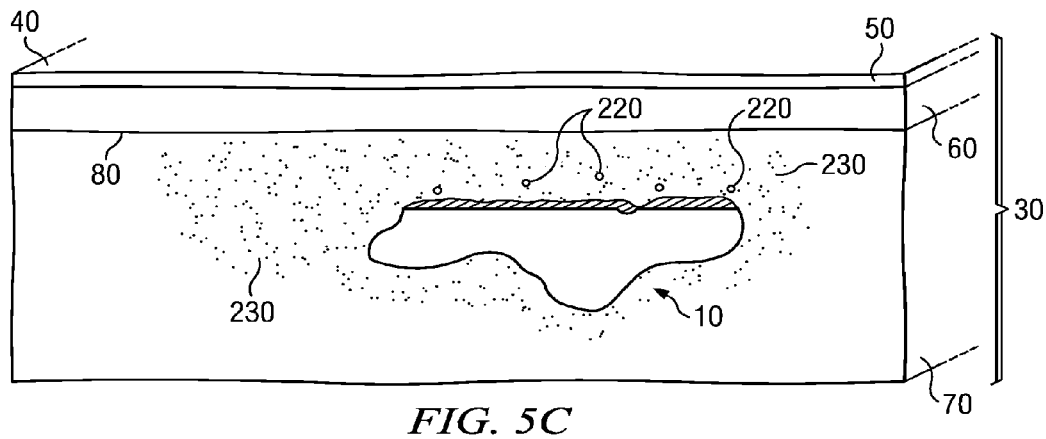
FIG. 5C is an illustration of the tattoo portion shown in FIG. 5B after about twenty minutes or more of waiting in accordance with prior tattoo procedures.

An exemplary laser pass and the R20 method is generally illustrated in FIGS. 5A, 5B, and 5C. As shown in FIG. 5A, light 200 from an emitter 210 penetrates the skin portion 30 and impacts the tattoo 10 within the dermis 70. As a result, bubbles 220 form. In addition, tattoo pigment dye 230 is released proximate the tattoo, e.g., from the destruction of phagocytosed or rephagocytosed cells of tattoo 10.

FIG. 5B illustrates the skin portion 30 following completion of the laser pass illustrated in FIG. 5A. As shown, there is an increase in the amount of dye 230 proximate the tattoo 10, as well as an increase in the number of bubbles 220.

If a subsequent laser pass would be performed upon the skin portion 30 as shown in FIG. 5B, such subsequent pass would be ineffective. As noted, for example, by Kossida et al., the administration of two passes separated by 30 seconds to 20 minutes has been tested and is not more effective than a single pass.

Accordingly, in the R20 method, to accomplish multiple laser passes, a delay of about 20 minutes or more is required for a skin portion to naturally resolve from an initial state as illustrated in FIG. 5B to a therapeutically more light-receptive state as illustrated in FIG. 5C (i.e., for example, a state including fewer bubbles 220, more dispersed dye 230, etc.). Put another way, while a skin portion 30 can go from FIG. 5A to FIG. 5B relatively quickly, for that same skin portion to go from FIG. 5B to FIG. 5C takes much longer, i.e., about 20 minutes or more.

The R20 process also is generally illustrated in the flowchart of FIG. 4. As shown, a single laser therapy session lasts from start 100 to end 140. In step 110, light therapy first is performed on a treatment area. Then, at step 120, the physician must wait for about 20 minutes or more for whitening reduction to occur naturally. After the delay, the treatment area assumes a therapeutically more light-receptive state, and the physician may choose at step 130 to end treatment (i.e., a one-pass laser session) or continue light therapy with another laser pass (i.e., a multiple-pass laser session). As shown in FIG. 4, in a multiple-pass laser session step 110, step 120, and step 130 are repeated until the session ends at step 140.

As described in this disclosure, very rapid resolution of one or more whitening reactions and/or one or more whitening reaction results may be achieved in one or more treatment processes or steps including the use of a chemical. See, e.g., FIG. 6 and FIG. 7. Such treatment including chemical use eliminates, among other things, the problematic "WAIT" step of prior methods for tattoo lightening or removal (e.g., the R20 method). In that way, without limitation, such chemical and its use may be regarded as a treatment facilitator and facilitating step, respectively. Compare, e.g., FIG. 6 and FIG. 7 with FIG. 4 (stop sign/wait step in FIG. 4 only).

Figure 6:
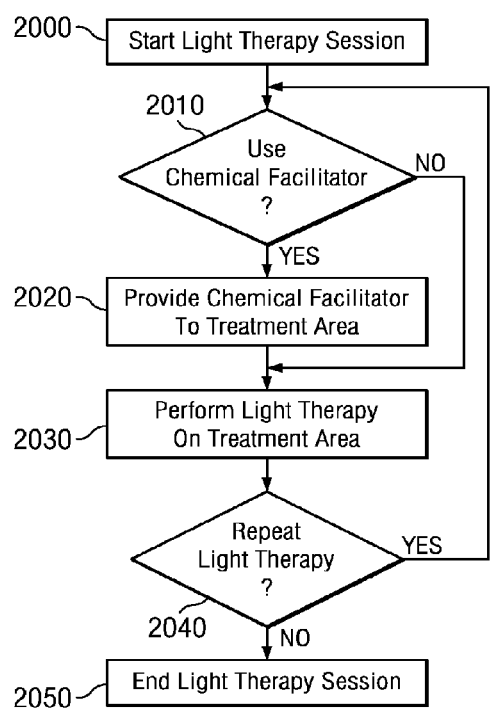
FIG. 6 is a flowchart of an exemplary embodiment of a light therapy session including use of a chemical facilitator.

As illustrated in FIG. 6, in one embodiment a light therapy session starts at step 2000 and ends at step 2050. First, a determination is made at step 2010 whether to use a chemical facilitator prior to light therapy. If no chemical facilitator is used, the method proceeds at step 2030 with a treatment area receiving light therapy. However, where a chemical facilitator is used, the method provides for step 2020, wherein a chemical facilitator is provided to the treatment area before the performance of light therapy step 2030. Following light therapy, the determination is made at step 2040 whether to provide additional light therapy treatment. If so, step 2010, step 2020, and step 2030, as well as step 2040, are repeated one or more times. The therapy session ends at step 2050 when it is determined at step 2040 that no further light therapy is to be provided during the session.

In accordance with the disclosure, variations on the embodiment illustrated in FIG. 6 may be used depending upon the circumstances involved in a particular application. For instance, one alternate embodiment is illustrated in FIG. 7.

Figure 7:
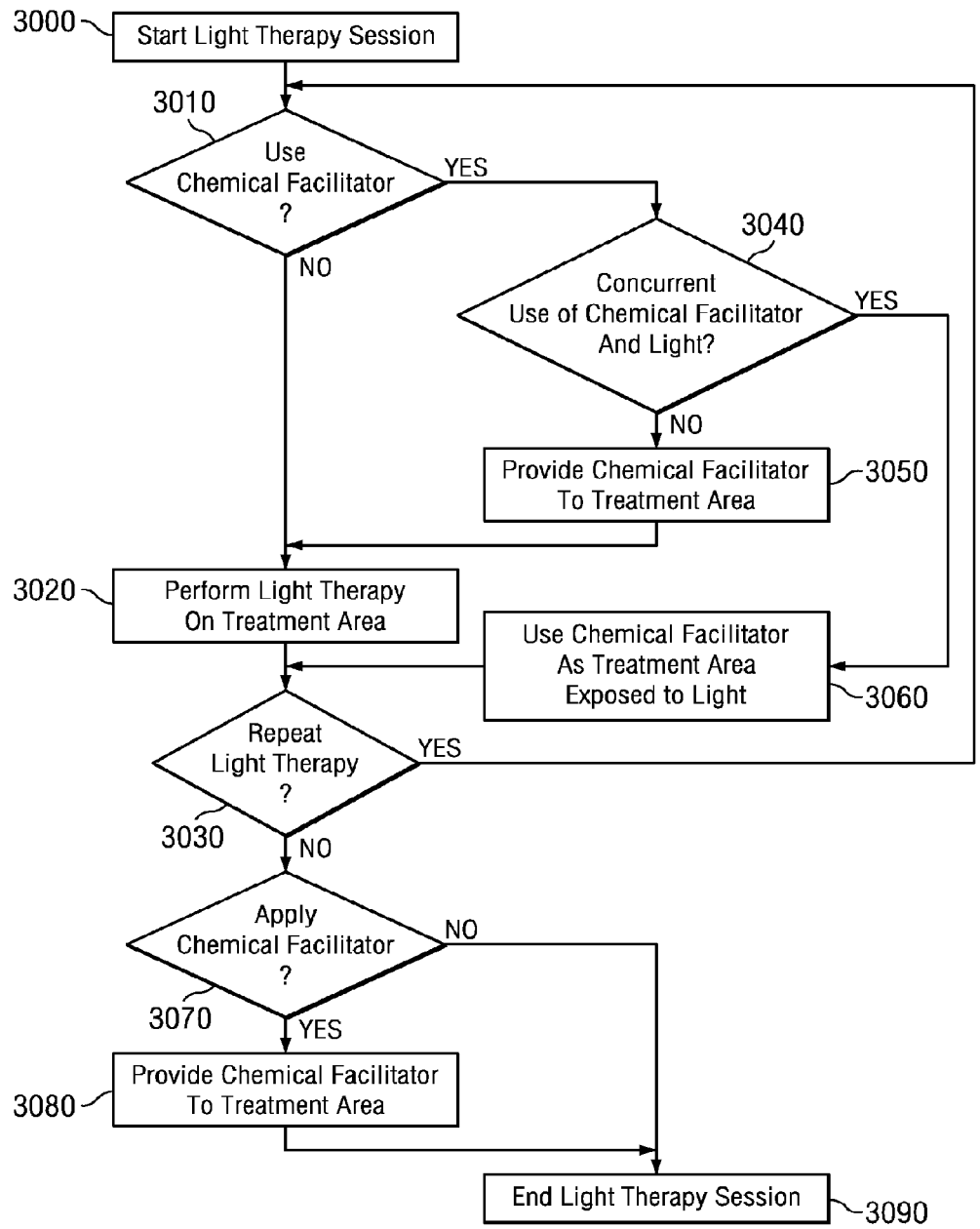
FIG. 7 is a flowchart of another exemplary embodiment of a light therapy session including use of a chemical facilitator.

As shown in FIG. 7, a laser therapy session extends from its start 3000 to its end 3090. An initial decision is made at step 3010 regarding use of a chemical facilitator (or not). The facilitator might be used, for example, to achieve a desired inhibition of whitening during a subsequent light therapy step. If no chemical facilitator is desired, light therapy is performed on a treatment area at step 3020. At that point, following light exposure, the determination is made at step 3030 whether additional light therapy is warranted for the treatment area. If so, a return to step 3010 follows.

Figure 10A:
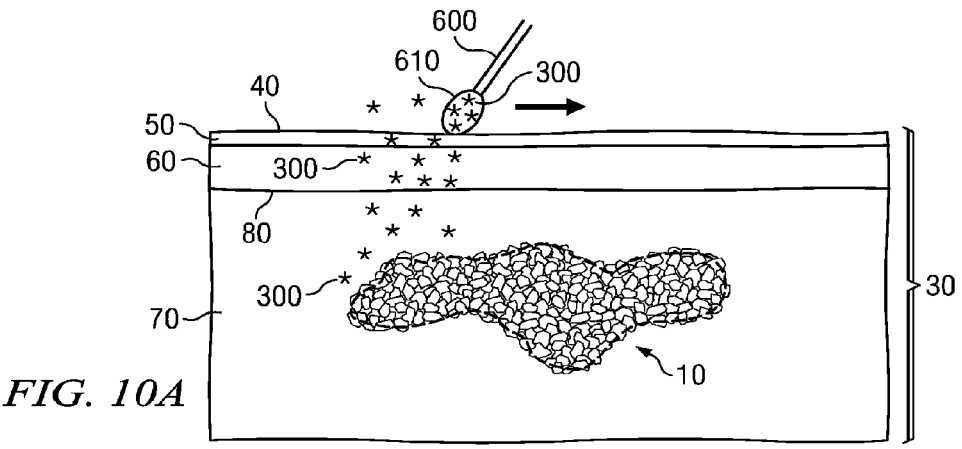
FIG. 10A is an illustration of another exemplary embodiment including use of perfluorodecalin for the exemplary tattoo shown in FIG. 3.
Figure 10B:
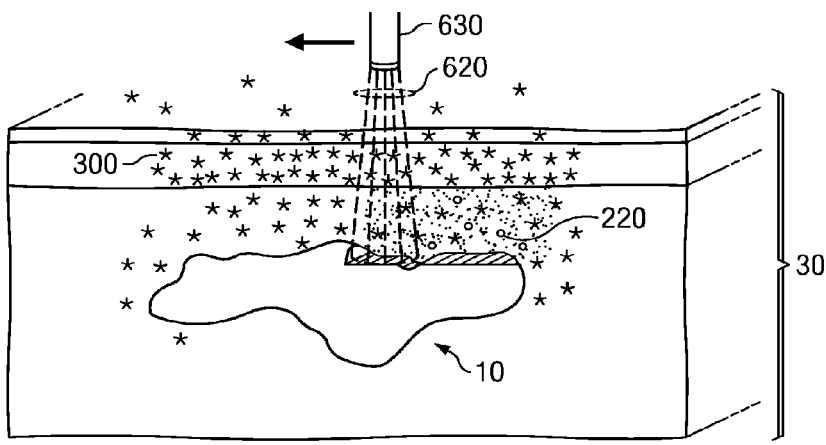
FIG. 10B is an illustration of an exemplary tattoo treatment including the exemplary embodiment shown in FIG. 10A.
Figure 11:
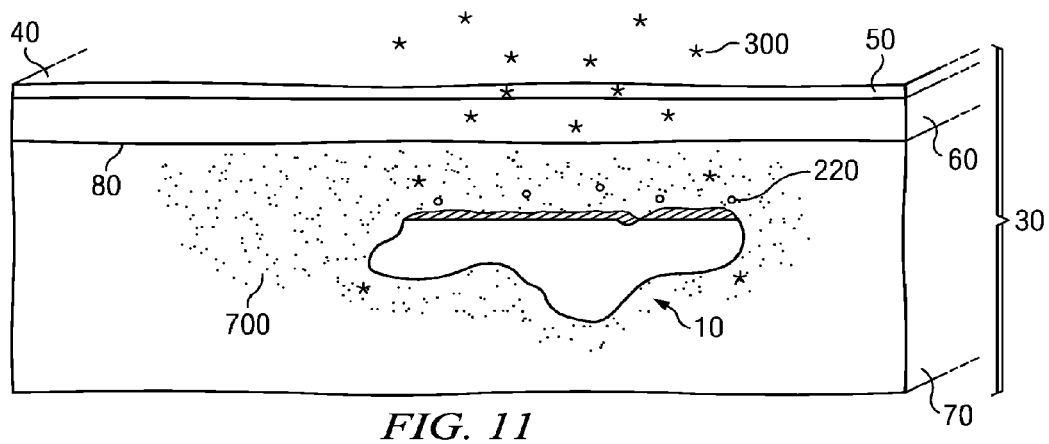
FIG. 11 is an illustration of the exemplary tattoo shown in FIG. 3 following an exemplary treatment including an embodiment of the disclosure.

If at step 3010 the determination is made to use a chemical facilitator, then a subsequent determination is made at step 3040 whether chemical facilitator use will occur concurrent with the application of light to the treatment area. If no concurrent use is planned, then chemical facilitator is provided to the treatment area at step 3050, and the method of the embodiment proceeds to step 3020. Where concurrent delivery of light and a chemical facilitator is not desired, application and delivery of chemical facilitator may occur at step 3050 prior to light exposure using an appropriate embodiment of the described system for the particular circumstances involved. One example of such an embodiment and its use for pre-treatment with chemical facilitator (e.g., before a laser use) is illustrated in FIGS. 10A and 10B.

Figure 9A:
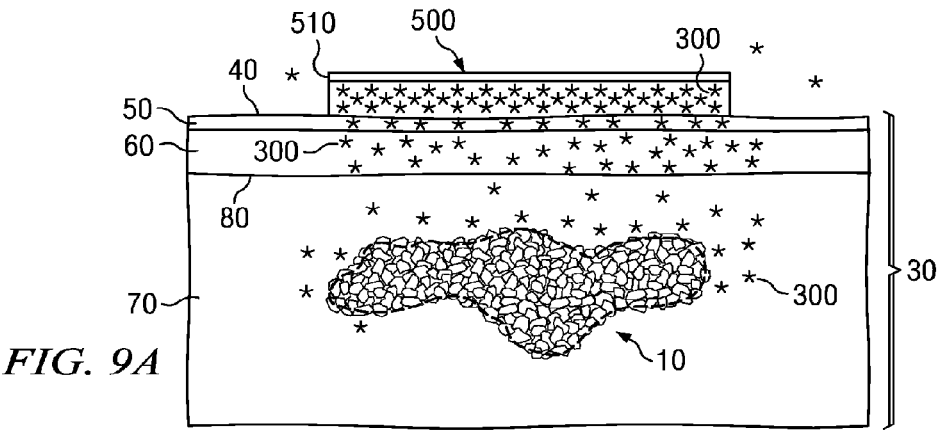
FIG. 9A is an illustration of an exemplary embodiment including use of perfluorodecalin for the exemplary tattoo shown in FIG. 3.
Figure 9B:
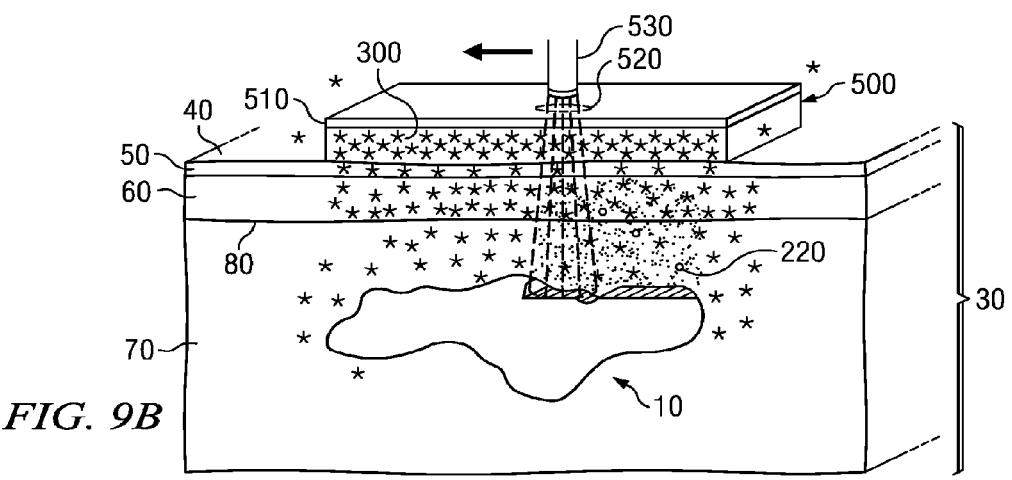
FIG. 9B is an illustration of an exemplary tattoo treatment including the exemplary embodiment shown in FIG. 9A.

At step 3040, however, if the determination is made to concurrently use a chemical facilitator and light therapy, then the method proceeds to step 3060 where the chemical facilitator is provided to a treatment area along with light. One exemplary embodiment of the disclosure that provides for concurrent delivery of chemical facilitator and light is illustrated in FIGS. 9A and 9B. Note, too, that depending upon the specific circumstances involved, such exemplary embodiment also is capable of providing a pre-treatment with a chemical facilitator prior to light exposure.

Following step 3020, and following step 3060, the exemplary method proceeds to step 3030, where a determination is made whether to provide additional light therapy to the treatment area. If no additional light therapy is required, the method proceeds to step 3070. At step 3070, a determination is made whether application or delivery of additional chemical facilitator to the treatment area is needed. Such additional chemical facilitator might be required, for example, to rapidly clear any remaining whitening effects before the end of the session at step 3090. Of course, the determination made will depend upon the circumstances involved in the specific treatment. If additional chemical facilitator is required, it is provided at facilitating step 3080 and the session then ends at step 3090; otherwise, the method proceeds from step 3070 to the end at step 3090.

In one embodiment, a chemical facilitator includes a fluorocarbon. In another embodiment, the chemical used includes a derivative of decalin. In another embodiment, the chemical used is an organic compound including fluorine in which 0-100% of hydrogen is replaced, e.g., by deuterium. In another embodiment, the chemical includes hydrofluorocarbons. In another embodiment, the chemical includes 1H-perfluoropentadecane (hentriacontafluoropentadecane). The chemical may include one or more of: (i) a fluorocarbon, (ii) a surfactant, (iii) a fluorosurfactant, and (iv) a non-hydrocarbon surfactant.

In one exemplary embodiment, very rapid resolution of whitening reaction results includes the use of a chemical including perfluorodecalin ($C_{10}F_{18}$). Perfluorodecalin is a fluorocarbon, and a derivative of decalin, in which all of the hydrogen atoms are replaced by fluorine atoms. Perfluorodecalin in general is regarded as chemically and biologically inert, and stable up to about 400° C. As more specifically described by Tsai, "Mike liquid perfluoro-n-alkanes (CnF2n+2, n=5-9) (Tsai, 2009), perfluorodecalin (C10F18) is a colorless, odorless, non-toxic, non-flammable, thermally stable, non-ozone-depleting, and heavy compound (high density and viscosity) with high volatility, low surface tension, high gas solubility, and very low solubility in water. Currently, it is primarily and increasingly used as a blood substitute (Lowe, 2008). In addition, it can be used as a contrast agent in a variety of diagnostic imaging techniques (e.g., ultrasound image) (Hall et al., 2000), temporary intraoperative vitreous substitutes in vitreoretinal surgery (ophthalmology) (Heimann et al., 2008), cosmetic and ointment additive for repairing burned skin and wound surface (Oxynoid et al., 1994), liquid ventilation used in the drug delivery (Kraft, 2001), carrier of glassified microspheres that contain vaccines (Coghlan, 2004), reaction medium in organic and organometallic syntheses (Hibbert et al., 1997; Sandford, 2003), volatile surfactant used for gas modification of lubricants and in optics and liquid lasers (Stoilov, 1998), and tracer gas in the environmental quality modeling in the ocean, and groundwater (Watson et al., 1987; Deeds et al., 1999)."

Figure 8:
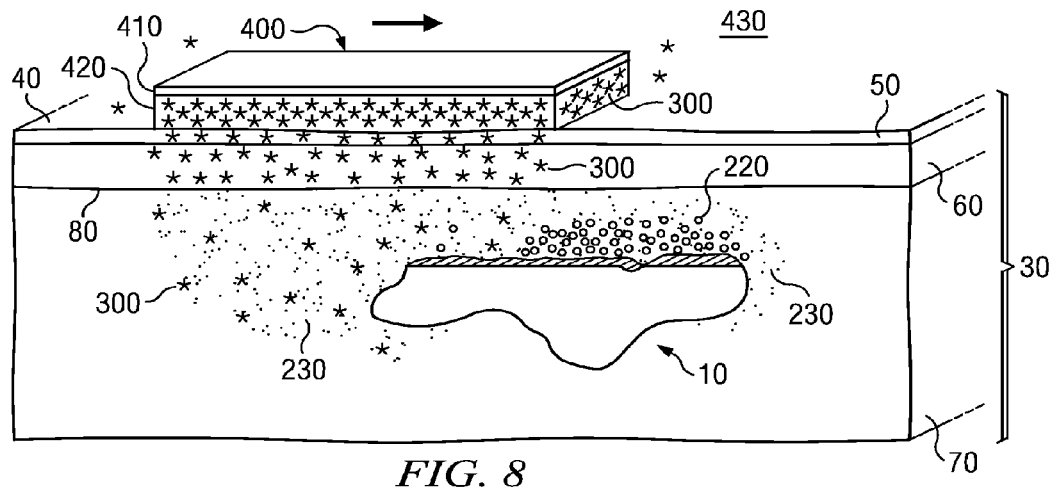
FIG. 8 is an illustration of an exemplary embodiment including use of perfluorodecalin against whitening of the type shown by way of example in FIG. 5B.

FIG. 8 illustrates an exemplary embodiment including perfluorodecalin delivery to a treatment area using a patch 400 including perfluordecalin 300. The patch 400 includes a first portion 410 and a second portion 420 including perfluorodecalin 300. As shown in FIG. 8, the patch is positioned on a skin surface 40, and perfluorodecalin has transferred from the patch 400 to an area and volume proximate the tattoo 10. As illustrated, perfluorodecalin may be present at various times not only proximate the tattoo 10, but also proximate the epidermis 60, the stratum corneum 50, and the environment 430 proximate the skin surface.

As illustrated in FIG. 8, as the patch 400 is moved across the skin portion 30 in an initial state following a laser pass (e.g., a state as shown for example in FIG. 5B), a very rapid, and perhaps almost instantaneous, reduction of whitening occurs, as evidenced by a reduction of the bubbles 220 associated with the transfer of perfluorodecalin from the patch 400 to an area proximate the tattoo and whitening.

In one embodiment, a patch or other chemical facilitator delivery means may be physically and/or physiologically similar to skin. Such means may be adapted for intimate contact with a patient; may be substantially optically transparent; and/or may be soothing, benign, comfortable, and/or pleasant in use. Further, the patch or other chemical facilitator delivery means may be cooperative, e.g., with skin or other aspects of a particular therapy, to help promote one or more result-effective events against one or more negative therapeutic effects.

The perfluorodecalin need not be applied to the treatment area using a patch, as illustrated for example in FIG. 8. Other chemical and facilitator delivery means also may be used, depending on the circumstances involved in a particular application. For instance, application of perfluorodecalin to a treatment area from a vial or other liquid container using a cotton swab has been shown to effectively resolve whitening in laser therapy within seconds. See the Pilot Study results included in this disclosure.

FIG. 9A illustrates an exemplary embodiment including prevention of an undesired whitening effect by using a patch including perfluorodecalin. As shown in FIG. 9B, a tattoo portion 10 is exposed to a light output 520 delivered through the patch 500. Prior to light exposure, the patch 500 is placed on a skin surface 40 proximate tattoo 10. The patch 500 includes a surface or region 510 that may be substantially impermeable to the perfluorodecalin 300. The region 510 may be within the interior of a patch, and/or the region 510 may form a portion or more of an outer surface of the patch. Perfluorodecalin in the patch 500 between the surface 510 and the skin surface 40 transfers into the skin portion 30 including tattoo 10. The patch may be optically transparent. The patch including perfluorodecalin also may be optically transparent.

In one embodiment, the patch 500 remains in place on the skin surface until a sufficient amount of perfluorodecalin 300 enters the skin portion 30 proximate the tattoo 10 to achieve a desired therapeutic result. A light output 520 from an emitter 530 is delivered through the patch 500 to treat the tattoo 10. See FIG. 9B. The emitter 530 may be moved as necessary across the patch to treat a desired skin area. The emitter 530 may be in contact with the surface 510, or may be spaced a distance from it. In an alternate embodiment, the patch 500 may be removed prior to laser therapy, so that light may directly impinge upon the skin portion 30 including perfluorodecalin 300 without passing through the patch 500.

As illustrated in FIG. 9B, perfluorodecalin proximate the tattoo portion treated effectively inhibits whitening due to the laser pass. The formation of bubbles 220 may be prevented in part, and/or rapid or near instant clearing of a substantial portion of formed bubbles may occur.

FIG. 10A and FIG. 10B illustrate another exemplary embodiment of the disclosure, including perfluorodecalin delivery to a treatment area using a swab including perfluorodecalin. The tip 610 of the swab 600 may include cotton or other suitable material to promote application or delivery of the perfluorodecalin 300. Perfluordecalin 300 may be provided to the swab tip 610 by immersing or otherwise contacting the tip 610 at least in part in a quantity of a perfluorodecalin-including substance (e.g., without limitation, a gel; liquid perfluorodecalin in a vial or other container or carrier; etc.). In one embodiment, the swab 600 itself may include perfluordecalin 300, e.g., in the tip itself, or in a chamber within the body of the swab 600. The chamber may be in, or be capable of being placed in, direct fluid communication with swab tip 610 or other delivery point. Of course, other configurations may be used too, as will be apparent to one of ordinary skill in the art having the benefit of this disclosure.

As shown in FIG. 10A, perfluorodecalin may be transferred to an area or volume proximate the tattoo 10 by moving the tip 610 including perfluorodecalin one or more times across a portion of the treatment area. Following such transfer, the swab or other perfluorodecalin delivery means may be removed, and a light output 620 from emitter 630 may be used to treat tattoo 10. Similar to the approach illustrated in FIG. 9A and FIG. 9B, delivery of the perfluorodecalin 300 proximate the tattoo 10 helps prevent undesired whitening following a laser pass. It is believed that whitening prevention may result from one or more factors, alone or in combination, including without limitation: the prevention of bubble formation, the rapid resolution of bubbles formed, and one or more other circumstances.

In one embodiment, perfluorodecalin is effective as a facilitator against whitening in a laser tattoo lightening or removal procedure. Regardless of the specific embodiment employed for facilitator delivery, use of a chemical facilitator against whitening may permit a physician to treat tattoos more rapidly than prior methods, e.g., substantially less than about twenty minutes or more between laser passes. Or, from another perspective, using prior tattoo treatment systems and methods, typically it takes about twenty minutes or more for a treatment site to transition from initial states (such as those as illustrated for example in FIG. 5A and FIG. 5B) to subsequent light-therapy-ready states (such as those as illustrated for example in FIG. 5C). Chemical facilitator use speeds such a transition.

Under the prior R20 and other treatment techniques, whitening due to a single laser pass diminishes over about 20 minutes or more. Treatment areas transition slowly from an initial state, and ultimately such areas naturally assume an improved state that generally is more receptive to laser treatment as compared to the initial state. Accordingly, the amount of total treatment time associated with prior R20 and other treatment techniques is quite significant.

In large measure, prior approaches are problematic due to the considerable waiting times required in every treatment session. Consider, for example, a physician having to wait twenty minutes following each single laser pass to continue a multiple pass laser treatment session. Such delay is inconvenient from a time-management perspective for both the physician and the patient. Further, the delay makes the management and flow of patients through the physician's office quite difficult, especially where a large number of patients may be treated each day, and also where waiting room and clinical space for performing therapeutic procedures is limited. Although the prior multiple pass method may provide greater efficacy as compared to a single pass method, the required lengthy treatment time may limit adoption of the prior multiple pass technique.

The invention and this disclosure effectively address this and other problems of prior methods. One exemplary embodiment relates to use of a facilitating step to cause a treatment area to assume more rapidly the same or a similarly receptive state for laser treatment. In some cases, the receptive state may be an improved or more receptive state from an optical and/or therapeutic perspective. The facilitator used may include a chemical, and the facilitating method portion may involve or include one or more steps including chemical use. The facilitator may be a chemical including perfluorodecalin. The chemical also may be a chemical not including perfluorodecalin. For clarity and convenience only, and without limitation, the Figures of this disclosure illustrate use of perfluorodecalin as a chemical facilitator. The invention and this disclosure, however, are not necessarily so limited. However, chemical facilitator use, and the performance of a facilitating step including chemical use, may enable treatment sites to transition much more rapidly from initial states (examples such initial states shown in FIGS. 8, 9A-B, and 10A-B) to later states (an example of such later states shown, e.g., in FIG. 11).

Although the specific treatment mechanism of action may involve multiple factors, it is believed that tattoo pigment heating may perform a role, due to the tattoo pigment including one or more metals and/or metal particles. Tattoo pigment heating may result in a scattering or intercellular dispersion of tattoo pigment to promote clearing. Cells including pigment (e.g., phagocytosed and/or rephagocytosed tattoo pigment particles) may be heated or otherwise treated to induce cell breakdown, destruction, or dispersion, that permits a clearing out of the tattoo pigment dye via the lymphatic system. See, e.g., FIG. 11, which illustrates dye 700 proximate tattoo 10 during laser treatment. Application of laser light rapidly increases local enthalpy, and accompanying this rapid heating and/or the other factors, almost instantaneous bubble formation may occur. Bubble formation, which often may be identified by a color change in the treatment area (e.g., a whitening) is generally regarded as undesirable, at least in part because bubble presence is thought to tend to inhibit optical penetration at the treatment site, and may result in a required interval of about twenty minutes or more between laser exposures and/or laser passes to allow the bubbles to resolve.

Direct or indirect delivery of a chemical to a treatment site via a carrier or other applicator assembly may promote resolution of whitening and/or other undesired conditions inhibiting treatment through one or more of: (i) reduction of local surface tension; (ii) gas absorption; (iii) penetration into tissue or skin; (iv) enhancement of gaseous diffusion (transcellular and/or otherwise); (v) migration or flow through tissue; (vi) refractive index matching; (vii) filling voids or gas-filled interstices; (viii) reduction of optical scattering; and (ix) optical clearing. These factors, and perhaps others, may relate to the observed very rapid resolution with the use of a chemical facilitator, such as one including perfluorodecalin. Perfluorodecalin, for instance, generally has excellent gas-carrying and gas-absorbtion properties, as demonstrated for example by its use in liquid breathing applications. Using perfluorodecalin, post-laser whitening resolution times of less than about thirty seconds, and more particularly of less than about five seconds, may be achieved. The actual time will depend of course on the specific circumstances involved in a particular application (e.g., size of the treatment area). Likewise, laser sessions for tattoo removal may take only a few minutes of total treatment time.

Resolution of conditions tending to inhibit treatment may be identified in various ways. In addition to accepted techniques for measurement of pertinent parameters (e.g., bubble size, density, count, dissolution), a color change generally characterized by a darkening of all or a portion of a whitened area may be observed. In some cases, a treatment area may resolve and turn from white to gray or black, or to the original color of the tattoo or portion treated. Rates of changes in color change, one or more parameters, etc., also may be identified.

In some laser treatments that include use of a R20 technique, the observed whitening (see, e.g., FIG. 5B as an exemplary illustration of such whitening) mostly goes away in 20 minutes, but there can be one or more areas (e.g., relatively small subsets of the treatment area) that resist and that do not resolve very well in that timeframe. However, if one were to wait much longer, i.e., for up to a month more (as in a typical treatment method that involves multiple treatment sessions over a period of months), such areas eventually would resolve substantially and most or all whitening would go away.

In one exemplary embodiment of this disclosure, the delivery of perfluorodecalin following one or more laser passes substantially eliminates such areas that otherwise (i.e., without perfluorodecalin use) would resist and not resolve very well in about twenty minutes. Accordingly, a tattoo treatment or procedure using perfluorodecalin as described herein may be more efficacious than R20 and other treatment techniques by providing rapid resolution of a substantially complete or entire treatment area (e.g., up to nearly 100% resolution, complete resolution), e.g., in a few minutes, in less than five minutes, almost instantaneously, more rapidly than R20, in a few seconds, in less than five seconds, etc., again depending upon the specific circumstances involved in a particular application.

Figure 12A:
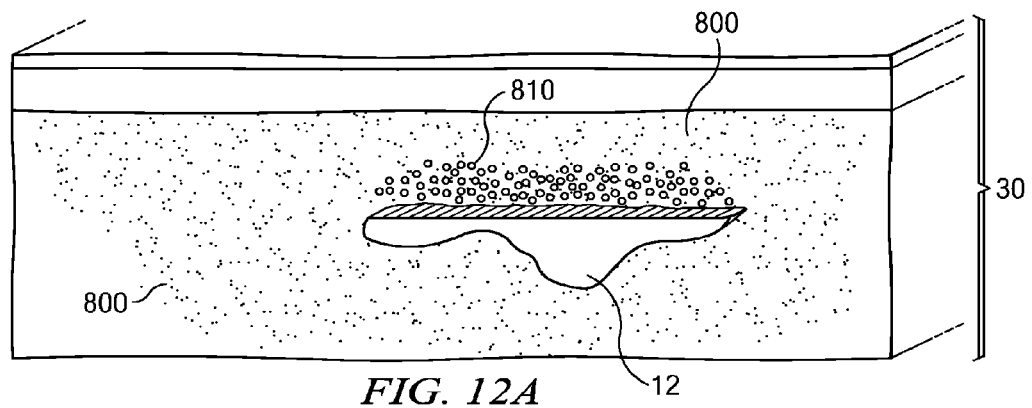
FIG. 12A is an illustration of the exemplary tattoo shown in FIG. 3, following an exemplary treatment, including more than one laser pass, and including whitening.
Figure 12B:
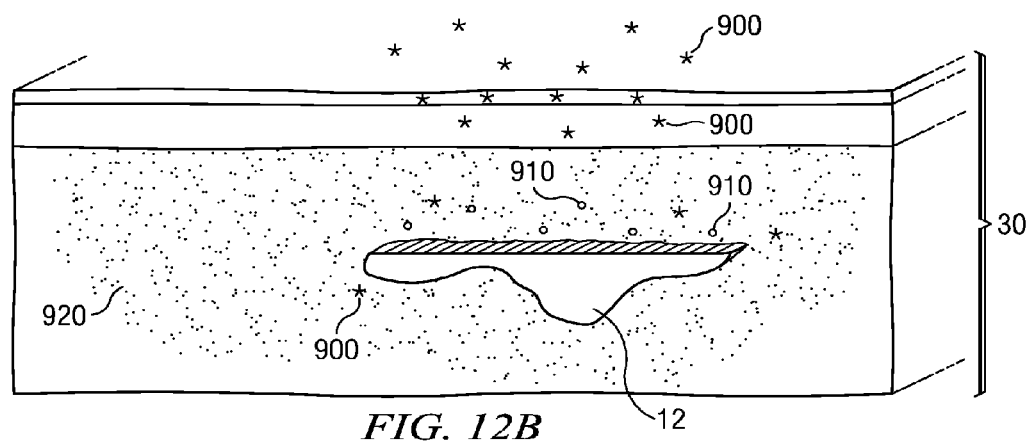
FIG. 12B is an illustration of the exemplary tattoo shown in FIG. 3, following an exemplary treatment, including more than one laser pass, and including use of an exemplary embodiment of the disclosure.

FIG. 12A illustrates a tattoo portion 12 during a multiple laser pass therapy session. More specifically, FIG. 12A illustrates the tattoo portion 12 in a state that may follow one of the later laser passes in a multiple pass therapy. As shown, significant amounts of dye 800, e.g., from phagocytosed cells including dye pigment, surrounds the tattoo 12, which is shown as being smaller in size than the tattoo 10 in the earlier Figures to reflect multiple laser passes. Considerable whitening is present, as evidenced by the large number of bubbles 810 at the treatment site. The absence of perfluorodecalin or any other facilitator in FIG. 12A might suggest, for example, that the last laser pass performed was completed without prior or concurrent use of a chemical facilitator. Had such a facilitator been used, a state more closely resembling the one shown in FIG. 12B would be expected (depending, of course, on the specific circumstances involved). In FIG. 12B, reduced whitening as compared to FIG. 12A is shown, as evidenced by relatively fewer bubbles 910, and some remaining facilitator 900 is present. As further shown, the amounts of dye 920 and the size of the treated tattoo portions 12 are somewhat similar in FIG. 12A and FIG. 12B, although that need not necessarily be the case. Indeed, use of a chemical facilitator may result in more effective therapy overall.

Figure 13A:
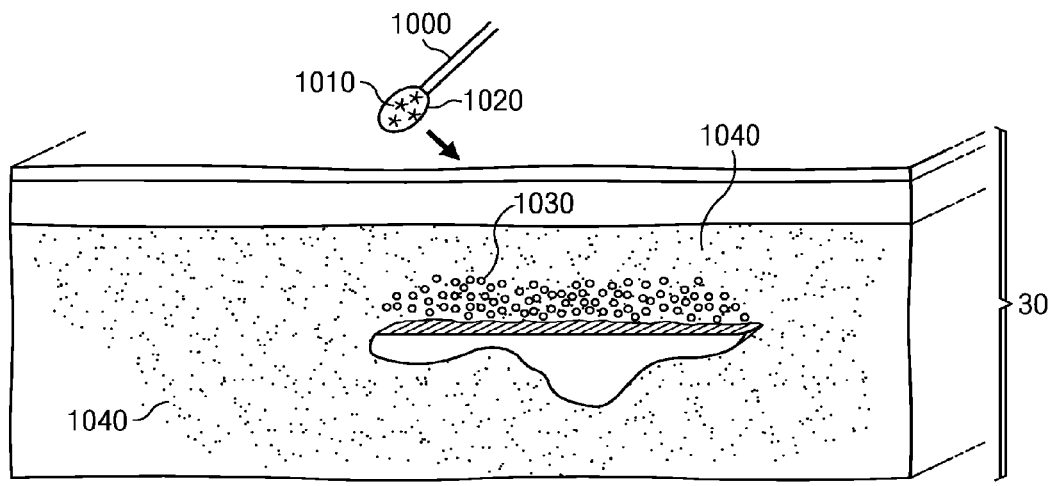
FIG. 13A is an illustration of the exemplary tattoo shown in FIG. 3, following an exemplary treatment, including more than one laser pass, and including use of an exemplary embodiment of the disclosure against whitening.
Figure 13B:
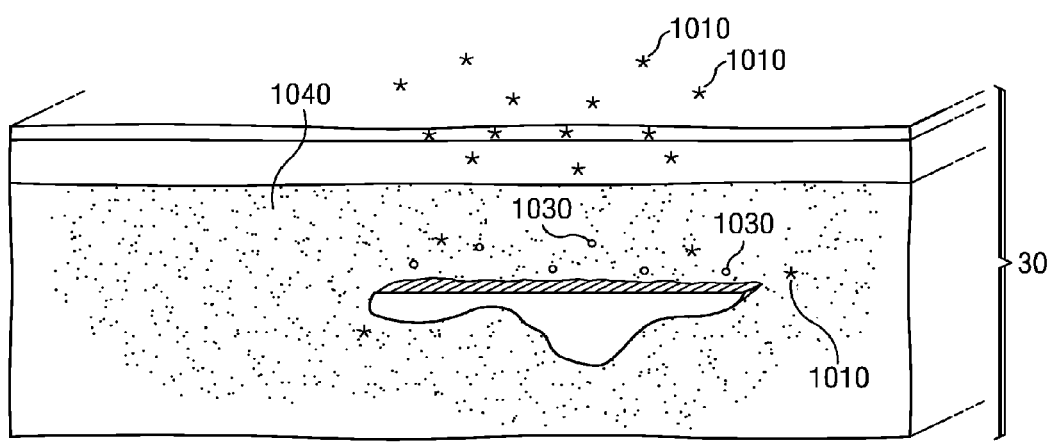
FIG. 13B is an illustration of the exemplary tattoo shown in FIG. 3, following an exemplary treatment, including more than one laser pass, and including use of an exemplary embodiment of the disclosure.

FIG. 13A illustrates one exemplary embodiment in which a swab 1000 including perfluorodecalin 1010 is used in a tattoo procedure including multiple laser passes and whitening. Perfluorodecalin 1010 from the swab tip 1020 is provided in sufficient quantity to a treatment area including bubbles 1030 and tattoo pigment dye 1040, so that whitening is substantially resolved. See FIG. 13B.

Perfluorodecalin use has an optical clearing effect. This effect may itself improve the efficacy of the system and method of the invention as compared to prior art techniques, e.g., those including a typical approach of "wait a month or more" or "wait 3-6 weeks" between laser treatment sessions, R20 methods, etc. Indeed, perfluorodecalin may facilitate laser treatment of any (or at least a wide variety of) generally undesirable conditions in the dermis (or elsewhere) for which laser treatment is used to promote the elimination or removal of such conditions in whole or in part. In one aspect, an exemplary embodiment of the invention includes eliminating at least in part an undesirable skin condition for which treatment with an emitter output promotes a therapeutic benefit, including: (a) delivering perfluorodecalin to an area of skin proximate the undesirable skin condition; and (b) exposing the area of skin to a therapeutic amount of an emitter output. A chemical facilitator other than one including perfluorodecalin may be selected for use based on its desirable characteristics (e.g., excellent skin penetrating ability, desired therapeutic results, and/or other factors). In some cases, the time between laser sessions may be substantially shortened to less than about 3-6 weeks with chemical facilitator use.

In accordance with one aspect of the disclosure, tattoo treatment may be achieved by pre-converting at least a portion of the blood proximate the tattoo to metHb prior to laser treatment. The "pre-conversion" to metHb prior to laser treatment may be achieved with the topical application of benzocaine and/or similar drugs. (For simplicity, only benzocaine shall be referred to herein, but the invention is not necessarily so limited.) The benzocaine penetrates the skin and chemically converts oxyhemoglobin ($HbO_2$) and deoxyhemoglobin (RHb) into methemoglobin (met-Hb) with efficiency and speed.

The pre-conversion of one or more hemoglobin species into metHb may bring the optical absorbance of the vessels in the treatment area into an effectively unchanging conformance, thus reducing or eliminating the possibility of sudden and unpredictable changes during laser treatment, and making adverse events and/or poor treatment outcomes less likely.

At some wavelengths, such as in the visible portion of the spectrum, metHb has a lower absorption than some other hemoglobin species. At other wavelengths, such as in the NIR (750 to roughly 1500 nm) metHb has a higher absorbance than most other hemoglobin derivatives. The unknown relative concentration of these hemoglobin species can grossly alter the response proximate the tattoo to a given optical treatment condition.

Benzocaine may be delivered in many ways, e.g., as a spray, a pre-treated wipe, a pre-filled applicator, a swab, a patch, or a topical cream. In one embodiment, a benzocaine delivery means like these or others supplies a controlled concentration of the drug to the treatment site (e.g., the patient's skin), so as to avoid the problems and potential adverse events associated with the application of uncontrolled concentrations. For example, benzocaine sprays and similar may induce methemoglobinemia under certain circumstances, a treatable (methylene blue injection or administration of oxygen) but cyanotic (asphyxiating) condition that is potentially life threatening, especially in newborns who have low circulating volumes of blood.

In accordance with one aspect of the present disclosure, a transparent flexible dressing or patch, comprising a lipid rich gel, may serve as a benzocaine delivery means. The gel includes a desired concentration of benzocaine. The concentration of benzocaine in the gel acts as a limit or check on the conversion to metHb, in that the amount of benzocaine delivered from use of the dressing or patch will not exceed the amount of benzocaine that is preloaded into the gel.

In accordance with one aspect of the disclosure, the benzocaine delivery means may comprise a flexible dressing or patch including a gel that is transparent to the output of the treatment laser. During treatment, a physician may leave the gel in place and fire the laser through it. Alternately, a physician may remove the gel prior to treatment laser use, and work on bare skin. Also, the physician may reapply the gel from time to time, as appropriate.

Similarly, perfluorodecalin may be delivered in many ways, e.g., as a spray, as a pre-treated wipe, as a prefilled applicator, in a patch, in a gel, with a swab, as topical cream. In one embodiment, a benzocaine delivery means, like such examples listed above or others, supplies a controlled concentration of perfluorodecalin to the treatment site (e.g., the patient's skin), so as to avoid any problems and potential adverse events associated with the application of uncontrolled concentrations.

In one aspect, in one embodiment of the disclosure including a lipid rich gel, the gel may include any non-polar, non-aqueous material. For example, gels including fats, fatty acids, mono- and poly-glycerides, glycol lipids, polyketides, glycerophospholipids, and sphingolipids may be used. In addition, lipid rich gel may be substances including non-polar, non-aqueous organics. Examples of such substances include, by way of example and without limitation, hexane, septane, nonane, naphtha, naphthalene, polyaromatic molecules, perfluorohydrocarbons, perfluorodecalin, freons, octane, n-hexane, and similar molecules.

In accordance with one aspect of the present disclosure, a transparent flexible dressing or patch, comprising a lipid rich gel, may serve as a perfluorodecalin delivery means. The gel includes a desired concentration of perfluorodecalin. The concentration of perfluorodecalin in the gel may act as a limit or check on the presence and/or amount of gas at the treatment site, and/or provide or promote enhanced optical clearing. A gel that is fully organic, mixed aqueous/organic and/or fully aqueous may serve as a carrier. Also, a gel may include an emulsion that includes one or more chemicals or substances of interest (i.e. perfluorodecalin).

In accordance with one aspect of the disclosure, the perfluorodecalin delivery means may comprise a flexible dressing or patch including a gel that is transparent to the output of the treatment laser. During treatment, a physician may leave the gel and/or dressing or patch in place and fire the laser through it. Alternately, a physician may remove the gel and/or dressing or patch prior to treatment laser use, and work on bare skin. Leaving the flexible dressing or patch in place may help reduce or confine the ejection or discharge of debris from the treatment site; defend against ejecta; ameliorate and/or eliminate unwanted conditions, etc., so as to help the clinician and/or patient, e.g., by acting as a shield; by collecting discharge; by absorption; by selective withdrawal or placement of substances; by cleaning, clearing, and/or containing a treatment area; by deflection, reflection, or the like; by beneficial scattering or redirection; by containment; by encapsulation; by disinfection; by removal; by transformation; and/or by delivering anesthetics, Gallenic topicals/drugs, or other patient comfort enhancing materials; etc. The patch may be used alone or in conjunction with a device to selectively perform, help perform, promote, and/or assist in the efficacy of one or more of the described desirable functions, processes, materials, etc.

In one exemplary embodiment, a carrier or applicator is provided. The carrier or applicator is adapted to be positioned proximate a skin treatment site. The carrier or applicator may include a flexible, transparent portion. A chemical including perfluorodecalin, another gas-absorbing chemical, or other chemical facilitator may be disposed between the flexible, transparent portion and the skin treatment site when the carrier or applicator is positioned proximate to the skin treatment site. In one embodiment, the flexible transparent portion may be disposed on a first side of the carrier or applicator, the first side being generally opposite from that portion of the carrier or applicator that may be in full or partial contact with the skin.

The flexible, transparent portion of the carrier or applicator may be substantially impermeable to perfluorodecalin (or other gas-absorbing or chemical facilitators) in its liquid state, in its gaseous state, or in both its liquid and gaseous states. Such portion of the carrier or applicator may tend to prevent the loss of perfluorodecalin or other chemical facilitators, e.g., due to evaporation. Moreover, as the flexible, transparent portion of the carrier and/or the perfluorodecalin and/or other chemical facilitator warms (e.g., with body temperature), the vapor pressure of the perfluorodecalin and/or other chemical facilitator will increase. Under such circumstances, the flexible, transparent portion of the carrier or applicator may further drive perfluorodecalin and/or other chemical facilitator into the skin treatment site, as both liquid and gas and all permutations of liquid only, gas only, and liquid plus gas.

In one embodiment, a system for the delivery of perfluorodecalin or other chemical facilitator to a skin treatment site may include means to promote driving perfluorodecalin or other chemical facilitator into the skin treatment site. Such means may include or provide, either alone or in combination, one or more of the following: vibration, ultrasound, heat, pressure, cooling, chemical gradient, and chemical action potential.

In another embodiment, a system for the delivery of perfluorodecalin or other chemical facilitator to a skin treatment site may include a patch or other device that is transparent to a laser output; that includes a top surface including a layer that is impervious to fluids; that is flexible and conformable to a portion of a patient's body; that includes a gel capable of hosting perfluorodecalin; and that includes a means to promote the temporary residence of perfluorodecalin in the gel. In one embodiment, the system may be rigid in part. In one embodiment, the system may include a release liner, foil pack, pouch, etc. to in whole or in part house the patch or other device prior to use with a patient, and to help promote the temporary residence of perfluorodecalin in the gel.

In another embodiment, a system and method for tattoo treatment includes delivery of perfluorodecalin or other chemical facilitator to a skin treatment site following pretreatment or preparation of the site. Pretreatment or preparation may include, alone or in combination, use proximate the skin treatment site of one or more of the following: a fractional laser; an ablative fractional laser; a non-ablative fractional laser; one or more micro-needle arrays; a heating apparatus, e.g., a heating pad or surface; a cooling apparatus for cooling a skin portion; a chemical, e.g., glycolic acid or dimethyl sulfoxide (DMSO). Pretreatment or preparation may tend to increase the permeability of a skin treatment site prior to the delivery of perfluordecalin to the site. Other pretreatments or preparations also may be used to create conditions to promote therapeutic benefit, e.g., cleaning the treatment area. A chemical facilitator, e.g., perfluorodecalin, also may be used in a pretreatment or preparation.

In another embodiment, a system and method for tattoo treatment includes delivery of perfluorodecalin or similar other chemical using a transport device for the chemical. The transport device generally promotes penetration of the perfluorodecalin or other chemical into the treatment area. Examples of transport devices include, without limitation: one or more needles, one or more syringes, a microneedle array, one or more injectors, glycolic acid, DMSO, penetrating oils, freons, iontophoretic transdermal systems, etc. that enhance transdermal transfer and/or permeability.

The optical power densities used to treat tattoos can be uncomfortable; pain may induce patient motion and distress, thus reducing calm, even proper optical delivery of the therapeutic laser beam by the operating physician. Thus, in accordance with one aspect of the disclosure, the administration of a drug for pre-conversion of one or more hemoglobin species into metHb, and/or the delivery of a chemical facilitator (e.g., perfluorodecalin), occurs along with the administration of an anaesthetic. In some cases, the pre-conversion drug may also serve as an anaesthetic, either alone or in conjunction with one or more other anaesthetic agents. Benzocaine, for example, is an effective pre-conversion drug that also is an effective topical anaesthetic (indeed, this is its formal indication for use). An anaesthetic agent, which may or may not promote pre-conversion, may be administered to patients in addition to perfluorodecalin (e.g., before, during, of after administration of perfluorodecalin).

Other dermatological conditions may benefit from treatment in accordance with one or more aspects of the disclosure, for example by changing (increasing or decreasing) the optical absorption of the treatment site (rendering it more susceptible to certain wavelengths of treatment light), reducing pain, or both. Such conditions and treatment sites include, without limitation, angiomas, hemangiomas, telangiectasias, varicosities, fine lines, wrinkles, scars, skin surface imperfections, areas of skin dispigmentation, freckles, age spots, solar lentigines, acne, hyperpigmentation, hypopigmentation, benign pigmented lesions, and other such or related conditions. Further, both the Title and the Abstract of this application are provided for convenience only, and should not necessarily limit the scope of the invention and disclosure.

In accordance with another aspect of the disclosure, in some embodiments it may be desirable to alter the preferential (selective) absorbance of one side of the vasculature in the sense of arterial vs. venous blood using the pre-conversion method described herein.

In accordance with another aspect of the disclosure, in some embodiments it may be desirable to treat background dyschromia (red or brown) by changing the absorbance of blood using the pre-conversion method described herein and also allowing use of more deeply penetrating wavelengths.

In accordance with one aspect of the disclosure, topicals and other agents that may promote the formation of metHb may be used. Many other topically applied substances can increase the local concentration of methemoglobin in the vasculature. Antibiotics, such as trimethoprim, sulfonamides and dapsone; local anesthetics, such as articaine, lidocaine and prilocaine; and other substances such as aniline dyes, metoclopramide, chlorates, bromates and nitrates, especially bismuth nitrate, can convert oxyhemoglobin and deoxyhemoglobin into methemoglobin.

Exemplary Treatment Systems and Methods:

The following are only a few exemplary embodiments of treatment systems and methods in accordance with the disclosure:

For Port Wine Stains:

Apply a small (roughly 2 $cm^2$) pad saturated with benzocaine, or up to 20% or more benzocaine, formulated so as to be lipophilic. Cover with an occlusive dressing for a few minutes. Discard dressing and clean off residue with an acetone wipe. Apply several coats of perfluorodecalin with a cotton-tipped applicator, working the perfluorodecalin in somewhat. Cover the benzocaine/perfluorodecalin-treated area with a transparent dressing or patch (cut to size). Fire the treatment laser through the transparent dressing or patch.

Laser selection: Q-switched alexandrite (755 nm) or Q-switched Nd:YAG (1064 nm). The objective is to get greater penetration depth in the NIR to treat the full thickness of the lesion. At optimal fluence, one pass in the NIR may be sufficient. Visible dye lasers also work, but because they are too strongly absorbed, they may treat too superficially.

Fluence: Start with a relatively low fluence. Increase as necessary to achieve a desired treatment. metHb has a higher absorbance in the NIR than $HbO_2$ or rHb. All three hemoglobin species have greater penetration depth in the NIR than in the visible.

For Tattoos:

The perfluorodecalin will have its best effect if it is degassed and appropriately delivered in a lipophilic gel dressing. In other words, it will assist in removing bubbles from areas of the tattoo that have been treated with a laser pulse, allowing greater penetration of subsequent treatment pulses without having to wait as long for the bubbles to be absorbed as would be the case with skin that has not been treated with perfluorodecalin. Perfluorodecalin can absorb considerable amounts of various gasses. Exposing degassed perfluorodecalin to atmospheric pressures for long periods of time will render it less effective. A transparent treatment patch composed of a suitable material such as a lipophilic gel preloaded with degassed perfluorodecalin or similar stored in a gas tight package until ready for application to the skin would assist in the speed of removal of tattoos by absorbing gas bubbles (or rendering them less troublesome) produced by the treatment laser light, said bubbles rendering the tissue less transparent to subsequent treatment laser light.

A chemical facilitator may be degassed in a variety of ways. One way is to expose it to reduced pressure or vacuum, allowing any dissolved gasses in the liquid to boil off and resulting in a lower vapor pressure of those gasses than in the tissue to be treated. A typical means would be to freeze the chemical facilitator into a solid, expose the solid to hard vacuum, and then slowly allow the solid to melt into a liquid so as to allow removal of dissolved gasses without excessive evaporation. This is the "freeze-pump-thaw" method.

Exposing the gel or system to partial pressures lower than those typically encountered within the tissue immediately following laser irradiation until the chemical facilitator alone, or in the gel or in the system fell below that within the tissue would result in a condition where gas would dissolve into the chemical facilitator from the tissue until an equilibrium condition was achieved. The lower the partial pressure of gas within the gel or system, the more gas that can be transferred from the tissue.

In one exemplary embodiment, then, a method for resolving whitening following laser therapy includes applying perfluorodecalin to a treatment area prior to exposure of the treatment area to a laser output, wherein the perfluorodecalin is in a partially degassed state when applied to the portion of the whitening.

For Neonates:

One of ordinary skill in the art, having the benefit of the present disclosure, will recognize the particular benefits of the disclosure for the treatment of neonates. Topical anesthetics in accordance with the disclosure, e.g., benzocaine (or similar), convert fetal hemoglobin to met fetal hemoglobin, so as to achieve one or more of the advantages described herein.

Use of Ultra-Short Pulses:

In accordance with one aspect of an exemplary embodiment of the disclosure, the system and method of the present disclosure include use of lasers with pulse widths shorter than one nanosecond, especially a few picoseconds or femtoseconds, which promotes treatment as a result of more rapid delivery of energy to the desired absorbers within a treatment site.

Super high energy, low power pulses may more effectively disrupt tattoo ink microspheres than lower energy high power pulses. In other words, picoseconds may be good, but femtoseconds may be better. Depositing all that energy instantaneously before the molecules can begin losing it as heat assures that the dye spheres will certainly fall apart, allowing the dye within the treatment site to diffuse into the tissue for intercellular clean up. Since tattoo dyes are complex materials, the energy also may tend to force them to decompose into smaller and/or more reactive species, which may also promote the clean-up process.

Pilot Study

Results of a pilot study related to the disclosure will be first released publicly in April 2012. The pilot study included tattoo removal with repeated laser exposures in one session, in which the need for 20-minute treatment intervals was eliminated. The pilot study was conducted at the Laser & Skin Surgery Center of New York (New York, N.Y.), under the direction of Roy G. Geronemus MD.

As background for the pilot study, tattoo removal in a single session with up to four repeated exposures each delivered after resolution of whitening had been demonstrated to be more effective than a single pass per session. A treatment delay of twenty minutes for resolution of whitening limited practicality of the technique, requiring up to eighty minutes of treatment time per visit. Medical grade, sterile perfluorodecalin, an inert, non-toxic liquid fluorocarbon with properties including optical clarity and gas-carrying capacity, was evaluated in the pilot study in an effort to speed resolution of cavitation-induced whitening immediately after laser treatment of tattoos. Perfluorodecalin may increase the optical penetration of lasers.

The pilot study was performed in consenting patients with unwanted tattoos. Each tattoo was treated in whole or part with topical perfluorodecalin by cotton swab prior to each laser pass. Lasers and settings were selected by a dermatologist. During and after treatments, extent and duration of whitening reaction was assessed as well as appearance of adverse effects, including pigmentary change or scarring. Each patient was seen at 3-6 weeks for follow-up and possible continued treatment.

In fifteen tattoos, perfluorodecalin was applied prior to each laser pass and the tattoo was treated with three Q-switched ruby laser passes immediately following one another in a single session. In five tattoos, a portion was treated with perfluorodecalin prior to a single pass of Q-switched ruby or Nd:YAG laser. All tattoos showed immediate whitening after laser treatment. After each laser pass, the whitening reaction resolved within five seconds of perfluorodecalin application. All treatments were well-tolerated with local anesthesia. Subjects reported normal to improved healing (amount of blistering, crusting or other changes) compared with previous treatments and no adverse effects occurred.

It was concluded that topical perfluorodecalin resolves post-laser whitening within seconds and permits safe immediate sequential treatment of tattoos in multiple passes (e.g., up to four passes) in a single session, allowing more effective tattoo removal in only a few minutes of treatment time (e.g., about 5 minutes, as compared to about 80 minutes with R20).

Definitions

The terms used herein and listed below have the meanings indicated below.

The term "HbO$_2$" means "oxyhemoglobin."
The term "RHb" means "deoxyhemoglobin."
The term "metHb" means "methemoglobin."
The term "NIR" means "near infrared."
The term "DMSO" means "dimethyl sulfoxide."

Other Exemplary Embodiments

Certain exemplary embodiments of the disclosure may be described as set forth in the claims below. Of course, the listing below (as well as each claim) may be modified in form and content, and the listing is not exhaustive, i.e., additional aspects of the disclosure, as well as additional embodiments, will be understood and may be set forth and claimed in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of treating a tissue volume including a skin portion comprising:
   (a) exposing the skin portion to one or more applications of light from a light-generating device to achieve a desired therapeutic result in the absence of promoting a photodynamic chemical reaction; and
   (b) providing a perfluorocarbon to the tissue volume before, during, or after step (a).

2. The method of claim 1, wherein the perfluorocarbon includes a derivative of decalin.

3. The method of claim 1, wherein the perfluorocarbon includes perfluorodecalin.

4. The method of claim 1, wherein each application of light includes a plurality of light pulses.

5. The method of claim 1, wherein the desired therapeutic result includes ejection of a pigmented substance from the tissue volume.

6. The method of claim 1, wherein the one or more applications of light include one or more laser sessions.

7. The method of claim 6, wherein the laser sessions are about four weeks apart.

8. The method of claim 1, wherein each application of light includes a laser session.

9. The method of claim 8, wherein each laser session includes one or more laser passes.

10. A method of treating a tissue volume including a skin portion comprising:
    (a) exposing the skin portion to one or more applications of light from a light-generating device to achieve a desired therapeutic result in the absence of promoting a photodynamic chemical reaction;
    (b) providing a perfluorocarbon to the tissue volume before, during, or after step (a); and
    (c) providing cooling for the one or more applications of light.

11. The method of claim 10, wherein step (c) includes cooling of the skin portion.

12. The method of claim 10, wherein step (c) includes cooling of the perfluorocarbon.

13. The method of claim 10, wherein step (c) includes cooling of the light-generating device.

14. The method of claim 10, wherein step (c) includes cooling of a skin-contacting device.

15. The method of claim 10, wherein step (c) includes cooling of a patch.

16. A method of treating a tissue volume including a skin portion comprising:
    (a) exposing the skin portion to one or more applications of light from a light-generating device to achieve a desired therapeutic result in the absence of promoting a photodynamic chemical reaction; and
    (b) providing a perfluorocarbon from a patch or from a vial to the tissue volume before, during, or after step (a).

17. The method of claim 16, wherein the patch is optically transparent.

18. The method of claim 16, wherein the patch is moving across the skin portion.

19. A method of treating a tissue volume including a skin portion comprising:
    (a) exposing the skin portion to one or more applications of light from a light-generating device to achieve a desired therapeutic result in the absence of promoting a photodynamic chemical reaction; and
    (b) providing a perfluorocarbon from a patch to the tissue volume before, during, or after step (a),
    wherein the light-generating device includes an emitter, and the emitter is moved across the patch.

20. The method of claim 19, wherein the patch is disposed in a pouch prior to use.

21. The method of claim 19, wherein use of the patch results in a reduction of pain as compared to a treatment in which the patch is not used.

22. A method of treating a tissue volume including a skin portion comprising:

(a) exposing the skin portion to one or more applications of light from a light-generating device to achieve a desired therapeutic result in the absence of promoting a photodynamic chemical reaction; and (b) driving a perfluorocarbon into the tissue volume before, during, or after step (a).

23. The method of claim 22, wherein the step of driving the perfluorocarbon into the tissue volume includes using vibration.

24. The method of claim 22, wherein the step of driving the perfluorocarbon into the tissue volume includes using ultrasound.

25. The method of claim 22, wherein the step of driving the perfluorocarbon into the tissue volume includes using heat.

26. The method of claim 22, wherein the step of driving the perfluorocarbon into the tissue volume includes using pressure.

27. The method of claim 22, wherein the step of driving the perfluorocarbon into the tissue volume includes using cooling.

28. The method of claim 22, wherein the step of driving the perfluorocarbon into the tissue volume includes using a chemical gradient.

29. The method of claim 22, wherein the step of driving the perfluorocarbon into the tissue volume includes using a chemical action potential.

* * * * *